US00PP34551P2

(12) United States Plant Patent
Huang

(10) Patent No.: US PP34,551 P2
(45) Date of Patent: Sep. 6, 2022

(54) ***AGAVE* PLANT NAMED 'NCYU CHERRY'**

(50) Latin Name: *Agave tuberosa*
Varietal Denomination: NCYU Cherry

(71) Applicant: FOREPORT ENTERPRISES Co., Ltd., Taipei (TW)

(72) Inventor: Kuang-Liang Huang, Chiayi (TW)

(73) Assignee: FOREPORT ENTERPRISES Co., Ltd., Taipei (TW)

( * ) Notice: Subject to any disclaimer, the term of this patent is extended or adjusted under 35 U.S.C. 154(b) by 0 days.

(21) Appl. No.: 17/561,973

(22) Filed: Dec. 26, 2021

(51) Int. Cl.
*A01H 5/02* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373, 263.1
CPC ..... A01H 5/02; A01H 5/12
See application file for complete search history.

*Primary Examiner* — Kent L Bell
(74) *Attorney, Agent, or Firm* — C. Anne Whealy

(57) ABSTRACT

A new and distinct cultivar of *Agave* plant named 'NCYU Cherry', characterized by its upright plant habit; straight lanceolate-shaped leaves that are not twisting; numerous semi-double to double-type purplish red-colored flowers arranged on upright and strong flower scapes; pleasant fragrance; and good cut flower performance.

1 Drawing Sheet

Botanical designation: *Agave tuberosa.*
Cultivar denomination: 'NCYU CHERRY'.

CROSS-REFERENCED TO CLOSELY-RELATED APPLICATIONS & STATEMENT REGARDING PRIOR DISCLOSURES BY INVENTOR & APPLICANT/ASSIGNEE

A Taiwanese Plant Breeder's Rights application for the instant plant was filed by the Applicant/Assignee, Foreport Enterprises Co., Ltd. of Taipei, Taiwan on Dec. 4, 2013, application number 1020173. Foreign priority is not claimed to this application.

An European Plant Breeder's Rights application for the instant plant was filed by the Applicant/Assignee, Foreport Enterprises Co., Ltd. of Taipei, Taiwan on Aug. 12, 2021, application number 2021/2053. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Agave* plant, botanically known as *Agave tuberosa* (formerly referred to as *Polianthes tuberosa*) and hereinafter referred to by the name 'NCYU Cherry'.

The new *Agave* plant is a product of a planned breeding program conducted by the Inventor in Chiayi City, Taiwan.

The objective of the breeding program is to create relatively compact and upright *Agave* plants with attractive inflorescences.

The new *Agave* plant originated from a cross-pollination in July, 2011 in Chiayl City, Taiwan of a proprietary selection of *Agave tuberosa* identified as code number 59 #, not patented, as the female, or seed, parent with a proprietary selection of *Agave tuberosa* identified as code number 84E19, not patented, as the male, or pollen, parent. The new *Agave* plant was discovered and selected by the Inventor as a single flowering plant within the progeny of the stated cross-pollination in a controlled greenhouse environment in Chiayi City, Taiwan in November, 2011.

Asexual reproduction of the new *Agave* plant by divisions in a controlled environment in Puli, Taiwan since March, 2015 has shown that the unique features of this new *Agave* plant are stable and reproduced true to type in successive generations.

SUMMARY OF THE INVENTION

Plants of the new *Agave* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'NCYU Cherry'. These characteristics in combination distinguish 'NCYU Cherry' as a new and distinct *Agave* plant:

1. Upright plant habit.
2. Straight lanceolate-shaped leaves that are not twisting.
3. Numerous semi-double to double-type purplish red-colored flowers arranged on upright and strong flower scapes.
4. Pleasant fragrance.
5. Good cut flower performance.

Plants of the new *Agave* differ primarily from plants of the female parent selection in flower size as plants of the new *Agave* have larger flowers than plants of the female parent selection. In addition, plants of the new *Agave* are slightly taller than plants of the female parent selection.

Plants of the new *Agave* differ primarily from plants of the male parent selection in flower size as plants of the new *Agave* have smaller flowers than plants of the male parent selection. In addition, plants of the new *Agave* are taller than plants of the male parent selection.

Plants of the new *Agave* can be compared to plants of *Polianthes hybrida* 'Chia Nong Pink Sapphire', disclosed in U.S. Plant Pat. No. 26,460. In side-by-side comparisons, plants of the new *Agave* and 'Chia Nong Pink Sapphire' differ in the following characteristics:

1. Plants of the new *Agave* are shorter than plants of 'Chia Nong Pink Sapphire'.
2. Plants of the new *Agave* have smaller flowers than plants of 'Chia Nong Pink Sapphire'.
3. Plants of the new *Agave* and 'Chia Nong Pink Sapphire' differ in flower color as plants of the new *Agave* have purplish red-colored flowers whereas plants of 'Chia Nong Pink Sapphire' have light lilac pink-colored flowers.

BRIEF DESCRIPTION OF THE PHOTOGRAPH

The accompanying colored photograph illustrates the overall appearance of the new *Agave* plant showing the colors as true as it is reasonably possible to obtain in colored reproductions of this type. Colors in the photograph may differ slightly from the color values cited in the detailed botanical description which accurately describe the colors of the new *Agave* plant.

The photograph is a top perspective view of typical flowering plants of 'NCYU Cherry' grown in a ground bed.

DETAILED BOTANICAL DESCRIPTION

The aforementioned photograph and following observations, measurements and values describe plants grown during the late summer in ground beds in a glass-covered greenhouse in Lisse, The Netherlands and under cultural practices typical of commercial *Agave* production. During the production of the plants, day temperatures ranged from 20° C. to 27° C. and night temperatures ranged from 15° C. to 18° C. Plants were four months old when the photograph and description were taken. In the following description, color references are made to The Royal Horticultural Society Colour Chart, 2015 Edition, except where general terms of ordinary dictionary significance are used.

Botanical classification: *Agave tuberosa* 'NCYU Cherry'.

Parentage:

*Female, or seed, parent*.—Proprietary selection of *Agave tuberosa* identified as code number 59 #, not patented.

*Male, or pollen, parent*.—Proprietary selection of *Agave tuberosa* identified as code number 84E19, not patented.

Propagation:

*Type*.—By in vitro meristem culture.

*Time to initiate roots, summer*.—About 14 days at soil temperatures about 20° C. and ambient temperatures about 23° C.

*Time to produce a rooted plant, summer*.—About 25 days at soil temperatures about 20° C. and ambient temperatures about 23° C.

*Root description*.—Medium in thickness, fleshy; typically grey in color, actual color of the roots is dependent on substrate composition, water quality, fertilizers, substrate temperature and physiological age of roots.

*Rooting habit*.—Moderate branching; medium density.

Plant description:

*Plant form and growth habit*.—Herbaceous flowering perennial plant; upright plant habit with strong upright flower scapes; leaves and flowering stems basal; moderately vigorous growth habit and moderate growth rate.

*Plant height, soil level to top of foliar plane*.—About 34.5 cm.

*Plant height, soil level to top of floral plane*.—About 75 cm.

*Plant width* (*spread*).—About 46.5 cm.

Leaf description:

*Arrangement and appearance*.—Leaves arranged in a basal rosette and along flower scape; leaves simple and sessile.

*Leaf length*.—About 37.1 cm.

*Leaf width*.—About 2.8 cm.

*Shape*.—Lanceolate; straight, not twisting.

*Apex*.—Acuminate.

*Base*.—Decurrent.

*Margin*.—Entire.

*Texture and luster, upper surface*.—Smooth, glabrous; matte to slightly glossy.

*Texture and luster, lower surface*.—Smooth, glaucous; matte to slightly glossy.

*Venation pattern*.—Pinnate.

*Color*.—Developing leaves, upper and lower surfaces: Close to 137B to 137C. Fully expanded leaves, upper surface: Close to a blend of 138B and 138C; venation, close to 137A. Fully expanded leaves, lower surface: Close to a blend of 138A and 138B; venation, close to 143B; thin waxy layer, close to 191B.

Flower description:

*Flower type and flowering habit*.—Semi-double to double-type flowers arranged on terminal racemes supported by strong upright scapes; flowers face mostly outwardly; freely flowering habit with about 48 flowers developing per inflorescence.

*Fragrance*.—Moderate; pleasant and sweet.

*Natural flowering season*.—Plants begin flowering about 16 weeks after planting; flowering continuous during the late summer in The Netherlands.

*Postproduction longevity*.—Flowers last about 10 to 20 days on the plant and about 10 to 14 days as a cut flower; flowers persistent.

*Flower buds*.—Height: About 4.5 cm. Diameter: About 1 cm. Shape: Oblanceolate. Texture and luster: Smooth, glabrous; matte. Color: Close to 156C tinged with close to 70C; towards the base, close to 149B to 149C and towards the apex, tinged with close to 145A.

*Inflorescence height*.—About 37.4 cm.

*Inflorescence diameter*.—About 9.7 cm.

*Flower diameter*.—About 3.1 cm.

*Flower depth*.—About 3.8 cm.

*Flower throat diameter*.—About 4 mm.

*Flower tube length*.—About 3.1 cm.

*Flower tube diameter*.—About 6 mm.

*Perianth*.—Quantity and arrangement: Typically 11 to 13 segments arranged in about four whorls; lower 54% to 55% of the segments are fused into a tube; upper free part of segments flaring outwardly to recurving. Outer segment length: About 5 cm. Outer segment width: About 9 mm. Inner segment length: About 4.1 cm. Inner segment width: About 8 mm. Segment lobe shape: Narrowly oblanceolate. Segment apex: Acute. Segment margin: Entire. Segment texture and luster, upper surface: Smooth, glabrous; moderately velvety; matte to slightly glossy. Segment texture and luster, lower surface: Smooth, glabrous; slightly velvety; slightly glossy. Outer segment color: When opening, upper surface: Close to 60A; towards the base tinged with close to NN155A and at the apex, close to 157D. When opening, lower surface: Lighter than 182D; towards the apex, strongly tinged with close to 196D. Fully opened, upper surface: Close to 60A; towards the base, close to 60D and tinged with close to NN155C; at the apex, close to 157D; venation, similar to lamina color; with subsequent development, color becoming closer to N77D, towards the base, lighter than N77D and tinged with close to NN155A. Fully opened, lower surface: Close to 186C; at the apex, close to 157D; venation, similar to lamina color; with subsequent development, color becoming lighter than N77D with midvein, close to 155A and towards the base, tinged with close to 156C. Inner segment color: When opening, upper surface: Close to 59C; towards the base, close to 59D and at the apex, close to 157D; midvein, close to 155A. When opening, lower surface: Close to a blend of 63C and 185D and at the apex, close to 157D; midvein, close to 157A. Fully opened, upper surface: Close to 60C; towards the base, close to 59D and at the apex, close to 157D; midvein, close to NN155A; with subsequent development, color becoming closer to 77D and towards the base, lighter than 77D and tinged with close to NN155A. Fully opened, lower surface: Close to 186C and at the apex, close to 157D; midvein, close to NN155A; with subsequent development, color becoming closer to 186C to 186D and midvein, close to 155A.

*Peduncles* (*flower scapes*).—Length: About 73.6 cm. Diameter: About 7 mm. Aspect: Upright. Strength: Strong. Texture and luster: Smooth, glabrous; slightly glossy. Color: Close to 144A.

*Pedicels*.—Length: About 9 mm. Diameter: About 2 mm. Aspect: About 20° from peduncle axis. Strength: Moderately strong. Texture and luster: Smooth, glabrous; matte. Color: Close to 145C.

*Flower bracts* (*also referred to as cauline leaves*).—Arrangement: One at the base of the pedicel. Length: About 4.2 cm. Width: About 8 mm. Shape: Lanceolate. Apex: Narrowly acuminate. Base: Broadly cuneate. Margin: Entire. Texture and luster, upper and lower surfaces: Smooth, glabrous; matte. Color, upper and lower surfaces: Close to a blend of 150D and 154D; towards the margins and the apex, close to 144A.

*Reproductive organs*.—Stamens: Quantity per flower: If present, one. Filament length: About 6 mm. Filament color: Close to N155B. Anther shape: Narrowly oblong. Anther size: About 1.5 mm by 5 mm. Anther color: Close to 150C. Pollen amount: Scarce. Pollen color: Close to 154C. Pistils: Quantity per flower: If present, three. Pistil length: About 2 cm. Style length: About 1.8 cm. Style color: Close to 150D, N155B and NN155A. Stigma diameter: About 1.5 mm. Stigma shape: Club-shaped, irregular. Stigma color: Close to NN155C. Ovary color: Close to 145C.

*Seeds and fruits*.—To date, seed and fruit development have not been observed on plants of the new *Agave*.

Pathogen & pest resistance: To date, plants of the new *Agave* have not been noted to be resistant to pathogens and pests common to *Agave* plants.

Temperature tolerance: Plants of the new *Agave* have been observed to tolerate temperatures ranging from −6° C. to 37° C. and to be suitable for USDA Hardiness Zones 8 to 11.

It is claimed:

1. A new and distinct *Agave* plant named 'NCYU Cherry' as illustrated and described.

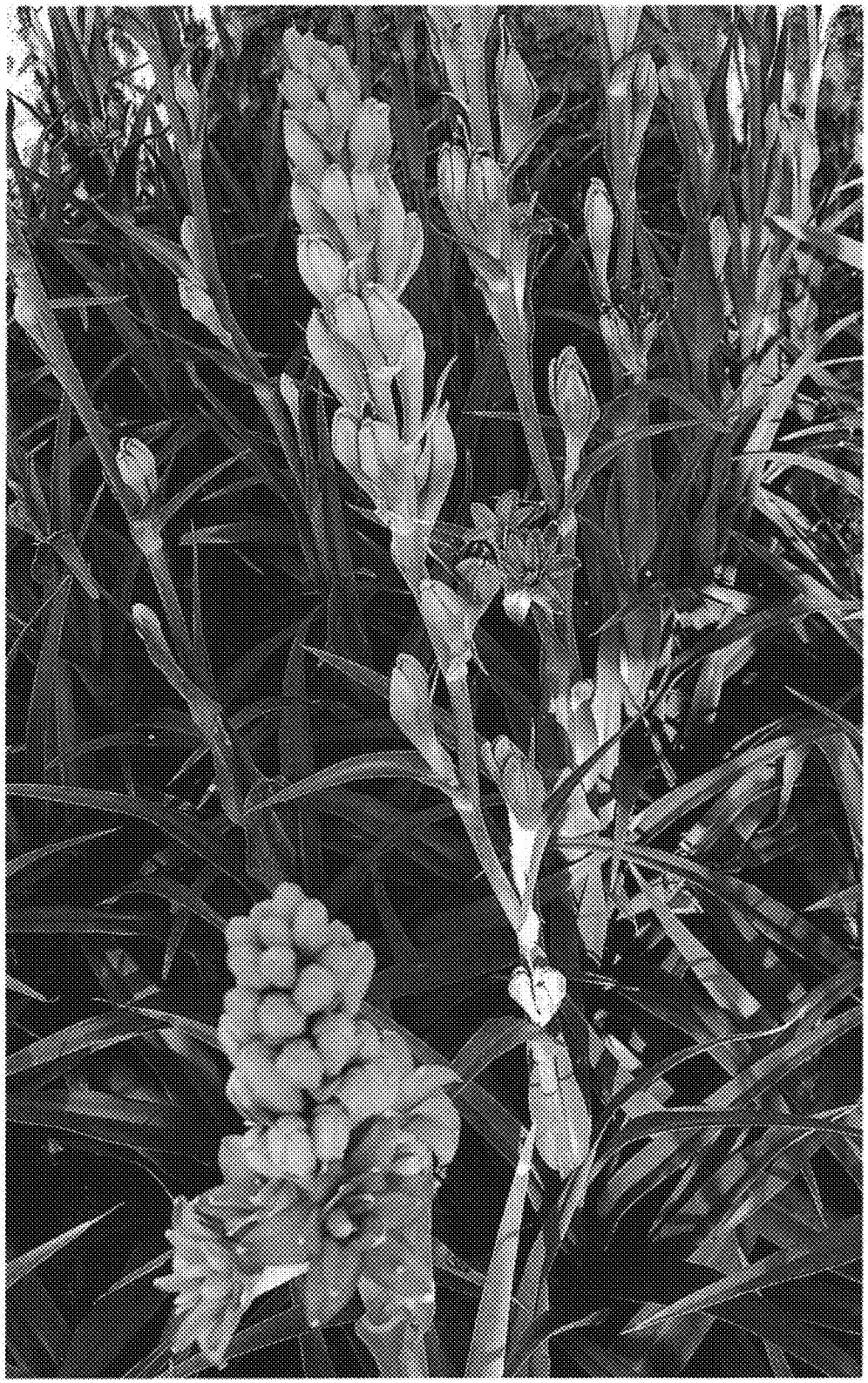

* * * * *